United States Patent [19]

Greer et al.

[11] 4,286,341
[45] Sep. 1, 1981

[54] VASCULAR PROSTHESIS AND METHOD OF MAKING THE SAME

[75] Inventors: Raymond T. Greer; Bradley H. Vale, both of Ames; Randall L. Knoll, Altoona, all of Iowa

[73] Assignee: Iowa State University Research Foundation, Inc., Ames, Iowa

[21] Appl. No.: 41,607

[22] Filed: May 23, 1979

Related U.S. Application Data

[63] Continuation-in-part of Ser. No. 30,146, Apr. 16, 1979, abandoned.

[51] Int. Cl.³ .............................................. A61F 1/24
[52] U.S. Cl. ............................................... 3/1.4; 3/1; 427/2
[58] Field of Search ............................ 3/1, 1.4; 427/2

[56] References Cited

U.S. PATENT DOCUMENTS

| | | | |
|---|---|---|---|
| 3,632,416 | 1/1972 | Shepherd | 3/1.4 X |
| 3,663,288 | 5/1972 | Miller | 3/1.4 X |
| 4,042,978 | 8/1977 | Jones | 3/1.4 X |
| 4,074,039 | 2/1978 | Lim | 3/1.4 X |
| 4,193,138 | 3/1980 | Okita | 3/1.4 |

*Primary Examiner*—Sidney Marantz
*Attorney, Agent, or Firm*—Tilton, Fallon, Lungmus et al.

[57] ABSTRACT

A vascular prosthesis and its method of fabrication. The prosthesis takes the form of a flexible and conformable support tube having a luminal surface formed of a smooth, homogenous, and substantially non-thrombogenic hydrogel having relatively small pores or microvoids suitable for tissue ingrowth but resistant to thrombus formation, and having an outer surface formed of essentially the same hydrogel having a heterogenous microstructure which includes relatively large pores or macrovoids especially suitable for cellular ingrowth from perigraft sources and attachment sites. In one embodiment, the tubular substrate is foraminous and the inner and outer hydrogel layers merge through the interstices of the substrate to provide a unified ground substance characterized by strata having selectively different pore characteristics for promoting effective endothelialization and for reducing possibilities of thrombotic occlusion.

34 Claims, 7 Drawing Figures

FIG. 1

VASCULAR PROSTHESIS AND METHOD OF MAKING THE SAME

RELATED APPLICATION

This application is a continuation-in-part of our co-pending application, Ser. No. 30,146, filed Apr. 16, 1979, and now abandoned.

BACKGROUND

Most vascular prostheses in current clinical use are formed of knitted or woven fabric with open interstices. Those interstices must be closed by thrombus, either before or after implantation. The tubular wall of such a prosthesis thus becomes sealed by a fabric-thrombus complex which is permeable to cellular ingrowth and which serves as the ground substance for subsequent endothelialization or healing of the graft. L. R. Sauvage et al., Surg. Clin. N. Am., 54:213-228 (1974).

In general, such grafts, whether woven or knitted, and whether formed of any of a variety of polymeric materials, have been used effectively only in connection with relatively large arteries (i.e., arteries having outside diameters of approximately 10 to 30 millimeters) such as, for example, the abdominal aorta and the aorto-iliac or aorta-femoral branches. Efforts to use such grafts, either as replacement or bypass grafts, with medium-sized arteries have been associated with a high incidence of delayed thrombotic occlusion, primarily because the whole blood thrombus which effectively seals the interstices of the graft is itself highly thrombogenic and causes additional thrombus which ultimately destroys the patency of the prosthesis. For the same reason, such grafts are regarded as totally unacceptable for small vessels (i.e., vessels having inside diameters less than about 8 millimeters).

While it has been suggested that problems of thrombotic occlusion might be avoided by forming the vascular prosthesis from a blood-tight biocompatible material, no such material meeting all of the requirements for an impervious graft (e.g., non-thrombogenic, highly conformable, readily suturable, an outer surface susceptible to tissue ingrowth, an inner surface to which any thrombus that does form can securely attach to discourage embolization, sufficient strength for easily withstanding hemodynamic pressures), has been reported. Some materials, such as expanded polytetrafluoroethylene, have met many of such requirements but, because of thrombogenicity or some other failing, have been found unacceptable. In the absence of an effective non-thrombogenic blood-impermeable material from which to form such a graft, the accepted approach has been to form vascular grafts from open mesh thrombogenic materials (polytetrafluoroethylene, polyethylene terephthalate, nylon, etc.) which depend for their effectiveness on thrombus formation (to render the grafts blood-tight) followed by endothelialization of the thrombus (to render the interior surfaces thrombus resistant). For reasons already given, the net result is that synthetic vascular prostheses are not currently available, or at least not recommended, as grafts for medium and small caliber vessels.

Even for larger caliber vascular grafts, where a porous thrombogenic material such as knitted polyethylene terephthalate (Dacron) has been commonly used, studies have revealed that only in relatively few cases do clinical grafts attain a completely healed flow surface, that is, a surface where cellular ingrowth has completely covered the luminal surface of the grafts to produce a continuous non-thrombogenic lining. While it has been suggested that some synthetic material of low thrombogenicity such as a hydrogel might be coated upon the luminal surfaces to insure a continuous thrombus-resistant lining, the absence of reports of successful experiments supports earlier appraisals that hydrogels, despite their desirable properties, do not have the mechanical strength and perhaps other requirements for effective use in vascular prostheses.

Additional references illustrative of the state of the art are: Greer, R. T., B. H. Vale, and R. L. Knoll, "Hydrogel Coatings and Impregnations in Silastic, Dacron, and Polyethylene," in *Scanning Electron Microscopy*, Vol. I, 1978, ed. by O. Johari, SEM Inc., Chicago, pp. 633-642; Ratner, B. D., A. S. Hoffman, "Radiation Grafted Hydrogels on Silicone Rubber as New Biomaterials," in *Biomedical Applications of Polymers*, ed. by H. P. Gregor, Plenum Publishing Corporation, New York, N. Y., pp. 159-171, 1975; Predecki, P., "A Method for Hydron Impregnation of Silicone Rubber, "*J. Biomedical Materials Research*, J. Biomed. Mater. Res. Vol. 8, pp. 487-489, 1974; Campbell, C. D., D. Goldfarb, and R. Roe, "A Small Arterial Substitute," *Ann. of Surg.*, Vol. 182, pp. 138-143, 1975; Ratner, B. D., and A. S. Hoffman, "Synthetic Hydrogels for Biomedical Applications," in *Hydrogels for Medical and Related Applications*, American Chemical Society Serial No. 31, ed. by J. D. Andrade, A.C.S., Washington, D. C., pp. 1-36, 1976; Lindenauer, S. M., T. R. Weber, T. A. Miller, S. R. Ramsburgh, C. A. Salles, S. P. Kahn, R. S. Wojtalik, "The Use of Velour as a Vascular Prosthesis," *Biomed. Eng.*, pp. 301-306, Sept. 1976; U.S. Pat. No. 2,976,576.

SUMMARY

One object of this invention lies in providing a synthetic vascular prosthesis which is suitable for use as a replacement or as a bypass for vessels of smaller sizes (under 10 millimeters inside diameter) as well as for larger sized vessels. More specifically, it is an object to provide an improved vascular prosthesis, and the method of forming such a prosthesis, in which the flow surface is of low thrombogenicity, thereby eliminating or greatly reducing problems of thrombotic occlusion, while at the same time having a stratified microstructure which promotes cellular ingrowth. A further object is to provide a reinforced vascular prosthesis in which the surface for contacing blood and other tissue are composed primarily of a synthetic biocompatible hydrogel and in which the porosity of such surfaces is varied to promote cellular ingrowth without at the same time providing a wall structure through which bleeding might occur. A still further object is to provide such a prosthesis in which a synthetic hydrogel, particularly a hydrogel based primarily on a sparingly cross-linked poly(hydroxyalkyl methacrylate), is integrated with a supporting tubular substrate to provide a reinforced composite structure suitable for implantation.

An aspect of this invention lies in recognizing that such a vascular prosthesis may be produced by coating the inner and outer surfaces of a tubular substrate with polymerizable mixtures of a water-soluble monolefinic monomer and a minor proportion of a water-soluble diolefinic cross-linking agent dissolved in a cosolvent system consisting essentially of water (or other constituent which is an effective solvent for the monomer but not for the polymer) and a water-miscible organic constituent which is an effective solvent for both the monomer and polymer, and controlling the water content of the solvent system for the respective coatings so that upon polymerization each coating will have a selectively distinctive microstructure. Ideally, both coatings or layers should merge within the interstices of the supporting structure, thereby providing an integrated and reinforced prosthesis in which the inner and outer surfaces are composed primarily of the same hydrogel with different pore characteristics. By controlling the proportions of constituents of the cosolvent systems during the steps of forming the prosthesis, the hydrogel layer along the inside of the graft may have a smooth homogenous microstructure with pores or microvoids well under 20 microns (Feret diameter), whereas the hydrogel of the outer layer may have a heterogenous microstructure which also includes macrovoids of a Feret diameter within the range of about 20 to 200 microns.

Other features, advantages, and objects of the invention will become apparent from the drawings and description.

DETAILED DESCRIPTION

The hydrogel used for coating or impregnating a tubular substrate to form a vascular prosthesis embodying this invention is a poly(hydroxyalkyl methacrylate) which is sparingly cross-linked to provide a resilient and essentially non-thrombogenic ground substance for controlled cellular ingrowth. Such a hydrogel has a microstructure of interconnecting pores and, as brought out hereinafter, by controlling the pore size at the luminal and outer strata of the graft, the tissue response and ingrowth characteristics may be controlled. While particularly effective results have been obtained with cross-linked poly(2-hydroxyethyl methacrylate) (P-HEMA), other synthetic hydrogels such as poly(glyceryl methacrylate) (P-GMA), poly(hydroxypropyl methacrylate) (P-HPMA), or poly(hydroxyalkyl acrylate) may be used.

The selected hydroxyalkyl methacrylate monomer is polymerized by irradiation, using a conventional $^{60}$Co source (or any other suitable radiation source such as electron irradiation, ultraviolet light irradiation, microwave irradiation, etc.), in the presence of a solvent system and a small amount of cross-linking agent. While ethylene glycol dimethacrylate (EGDMA) has been found particularly effective as a cross-linking agent, other well known cross linkers, including methylene-bis-acrylamide and derivatives of EGDMA, may be used. In general, the cross-linking agent should be present in the amount of between 1 to 20% by weight of the reaction mixture, the higher levels being appropriate where a comonomer such as n-vinyl-2-pyrrolidone is included to enhance water imbibition. Apart from the circumstance in which such a comonomer is used, the proportion of cross linker would ordinarily be within the range of about 1 to 5%. The monomer concentration should fall within the range of 5 to 40% and preferably within the range of 10 to 20%.

The substrate for the hydrogel takes the form of a support tube having an inside diameter within the range of about 1 to 30 millimeters and a wall thickness of approximately 0.5 to 1.5 millimeters. Wall thicknesses in the upper part of the range would normally be used with vessels of larger diameter, so that with vessels under 10 millimeters inside diameter (i.e., vessels of a size for which vascular prostheses are not known to have been available and for which this invention is particularly suitable), the wall thickness would ordinarily be under 1 millimeter.

A support tube constructed of a mesh of polyethylene terephthalate (Dacron) has been found effective, although any of a variety of porous and non-porous materials might be used. A mesh or porous structure is ideally suited because the foraminous network permits a continuous impregnation of the wall structure by the hydrophilic gel which serves as the ground substance for tissue ingrowth, and because such a gel/substrate interrelationship insures a secure support for the hydrogel during the healing period of cellular invasion. Where a mesh structure is utilized, the tube may be of a fibrous nature with the filaments thereof being interlocked in a woven, knitted, or non-woven fabric. The open pores or interstices of such a fabric should be of a size within the general range of about 50 to 400 microns.

The substrate materials suitable for use in fabricating the support tube may include, in addition to polyethylene terephthalate, such materials as polytetrafluoroethylene, silicone rubber, poly-E-caprolactone, polyethylene, and biodegradable polymers such as poly(glycolic acid), poly(lactic acid), and poly(hydroxy butyric acid). Poly-E-caprolactone has a relatively low melting point (about 60° C.) and has the advantage of permitting size adjustments during a surgical procedure (by heating the prosthesis in a water bath) to achieve close matching of the diameter of the graft to the natural vessel to be secured thereto. The use of biodegradable polymers permits cellular invasion of the prosthesis to be followed by complete replacement of the synthetic material by natural tissue.

Where the support tube is formed of woven material, it is particularly desirable if the fabric is warp knitted to provide a velour (loops of yarn extending perpendicularly from the fabric surface) along at least the outer surface of the tube. A double velour, one in which such loops are provided along both the inner and outer surfaces of the support tube, is believed particularly effective with larger-sized vessels having inside diameters of 10 millimeters or more. In either case, the velour promotes secure attachment between the tubular substrate and the hydrophilic gel supported by that substrate.

The hydrogel layers which define the inner and outer surfaces of the final prosthesis are of the same composition but of different porosity. Specifically, the maximum Feret diameter, using the procedure described by de-Hoff and Rhines in Quantitative Microscopy, 340–341 (McGraw Hill), of the pores or voids along the luminal surface of the prosthesis should be well under 20 microns and preferably within the range of 0.1 to 10 microns. On the other hand, the hydrogel layer along the outside of the prosthesis should have, in addition to the microvoids of under 20 microns already described, larger pores or macrovoids of Feret diameters within the range of 20 to 200 microns, and preferably above 30 microns. The result is a prosthesis in which the hydrogel along the outer surface is heterogenous, having macrovoids particularly well suited for the rapid ingrowth or perigraft tissue, and in which the same hydrogel composition along the inner surface is relatively smooth and homogenous in character, having micropores small enough to prevent the escape of blood elements while at the same time being conducive to cellular ingrowth. Ideally, the inner and outer hydrogel coatings or layers are simply exposed portions of the same hydrogel composition which impregnates the full wall thickness of the tubular substrate.

Figure 1:
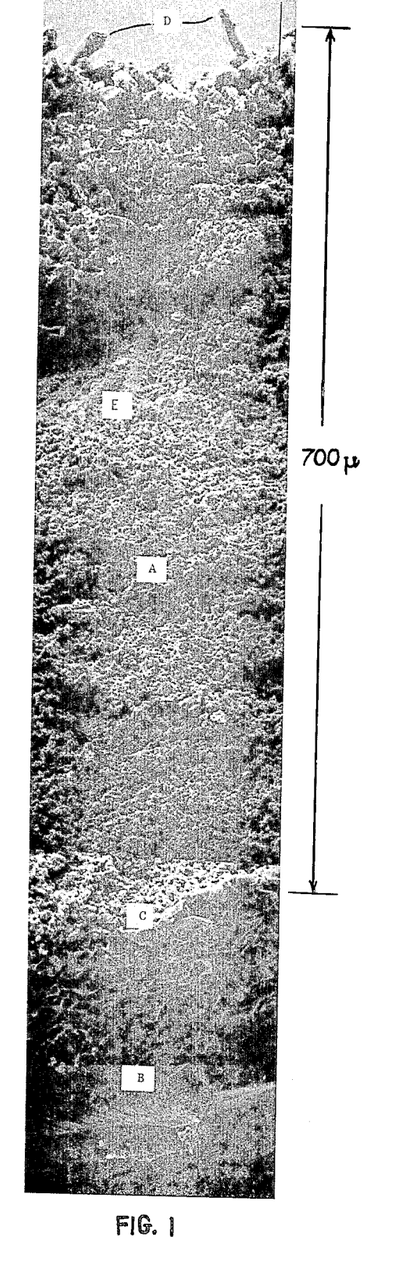
FIG. 1 is a composite of scanning electron micrographs showing a cross section of the wall of a polyethylene terephthalate (Dacron) vascular prosthesis with a poly(hydroxyalkyl methacrylate) hydrogel of selectively controlled and differing microstructure impregnating the interstices thereof.

The microstructure of such a prosthesis is illustrated photographically in FIG. 1. That figure is a composite of several scanning electron micrographs showing a small cross section of the wall of a vascular prosthesis embodying this invention. The wall A is shown to have a thickness of approximately 0.7 millimeters (700 microns), as indicated by the 50 micron scale bar shown at top right. The generally smooth area B shown near the bottom is the inside surface of the tubular prosthesis, that surface terminating, and the cross section beginning, along a transition line C.

The prosthesis of FIG. 1 is formed of a knitted Dacron support tube having an external velour and completely impregnated with a P-HEMA based hydrogel. The outside surface of the prosthesis is shown near the top with letter D designating the hydrogel-coated fibrils of the velour fabric. At various points such as, for example, at E, the filaments of the knitted support tube are faintly visible. Almost the entire cross sectional area represented by A is filled with a heterogenous hydrogel having random macrovoids of Feret diameters ranging between 20 to 40 microns as well as microvoids having Feret diameters within the range of 0.001 to 1.0 microns. At the bottom, in zone B, the macrovoids are virtually absent, the microstructure having a more homogenous appearance with micropores of a maximum Feret diameter less than 1 micron. At the merger of the homogenous layer with the heterogenous layer, there appears to be a penetration of the former into the latter a distance of approximately 20 to 30 microns; that is, the homogenous layer extends a limited distance into the macrovoids of the heterogenous layer.

The differences in the microstructure of the hydrogel within the inner and outer layers of the prosthesis are achieved by forming the hydrogel upon (and preferably within) the wall of the tubular substrate in at least two steps, and by varying the solvent systems used in the respective polymerization steps. In the prosthesis depicted in FIG. 1, for example, the hydrogel impregnating the wall of the tubular substrate is formed in two polymerization steps, each step involving 20% HEMA by volume as the monomer and 3% EGDMA by volume as the cross-linking agent, the remainder of the polymerization mixture being composed of a methanol/water solvent media. For each layer, polymerization was initiated by the same level (megarads) of radiation (0.25 Mrad of $^{60}Co$). The differences in microstructure were produced by the fact that the proportions of water and methanol in the respective solvents were different. Specifically, the smooth homogenous hydrogel layer B was produced using a solvent composed of 50% methanol and 50% water, whereas the coarse heterogenous layer was formed with a solvent composed of 25% methanol and 75% water, measured on a volume basis. On a weight percentage basis, the smooth homogenous hydrogel of layer B was formed in a solvent system containing 32.6% methanol and 41.2% water, the monomer being 22.9%, and the cross-linker being 3.3%. By contrast, the weight percentages for the heterogenous layer were 15.7% methanol, 59.2% water, 21.9% monomer, and 3.2% cross-linker.

The presence or absence of macrovoids result from the fact that one of the components of the cosolvent system (water) is a non-solvent for P-HEMA whereas the other component (methanol), as well as the HEMA monomer itself, are solvents for the polymer. If the percentage of water by weight for the entire polymerizable mixture (including solvent) exceeds about 45%, then the polymerization reaction continues in a precipitating medium to produce an opaque spongy heterogenous gel characterized by macrovoids as well as microvoids, whereas if the percentage of water in the solvent system remains below the critical level of approximately 45%, the reaction continues in a solvent medium and a transparent homogenous gel having only microvoids will be formed. In addition to the proportion of water in the solvent system, the conditions of formulation of a homogenous or heterogenous polymer may also be influenced by the amount of cross-linking agent present in the system. That influence is, however, much less significant in affecting the microstructure than that of the solvent, especially if the hydroxyalkyl methacrylate monomer is at a concentration of 10% or more, since the difference in the affincity towards water between the monomer and the cross-linking agent is not too marked.

Other solvents may be substituted for the methanol moiety of the cosolvent system such as, for example, ethanol, dimethyl sulfoxide, dimethyl formamide, tetrahydrofuryl alcohol, ethylene glycol monomethyl ether, ethylene glycol monoethyl ether, 2,2,3,3-tetrafluoropropanol, and other strongly polar solvents for both the monomer and the polymer. Whatever cosolvent is selected, that solvent should of course be compatible (miscible) with water.

While water has been described as an important constituent in the cosolvent medium, other cosolvents which have the similar properties of being solvents for the monomer and non-solvents for the polymer, and of being miscible with the other cosolvent of the system, might be used. For example, 1-butanol may be substituted for water in a solvent system, in which case dioxane may be used as a suitable cosolvent. It has been found that such constituents in a dioxane/1-butanol system function in a manner similar to the constituents in a methanol/water system with the transition point between homogenous and heterogenous gels developing at about 45% by weight of that constituent of the cosolvent medium (i.e., 1-butanol) which is a solvent for the monomer and a non-solvent for the polymer.

Figures 2, 3, 3A, 4, 4A, 5:
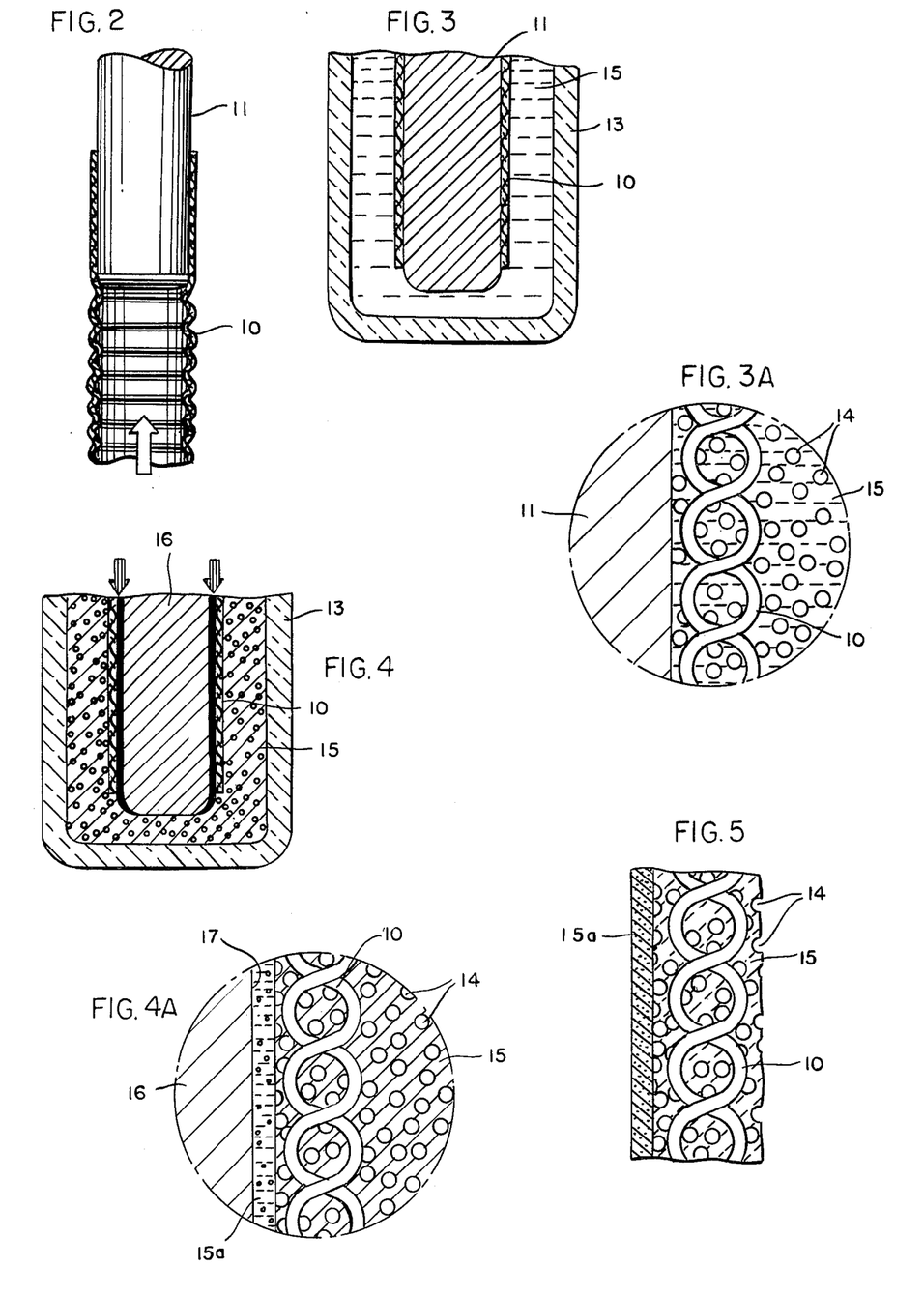
FIG. 2 is a somewhat schematic cross sectional view illustrating a first step in a method of forming a vascular prosthesis embodying the invention.
FIG. 3 is a fragmentary sectional view illustrating a second step in the method.
FIG. 3A is a greatly enlarged schematic view of an indicated portion of FIG. 3.
FIG. 4 is a fragmentary sectional view indicating a further step in the method of the invention.
FIG. 4A is a greatly enlarged fragmentary schematic view of an indicated portion of FIG. 4.
FIG. 5 is an enlarged schematic cross sectional view of a wall portion of a vascular prosthesis formed in accordance with the method of this invention.

The method steps by which a tubular substrate may be internally and externally coated with a porous water-imbibing gel having selectively different microstructures along the respective surfaces is schematically illustrated in FIGS. 2 through 5. In FIG. 2, a support tube 10 is shown being fitted upon an inert rod 11 of glass, Teflon, or other suitable material. The support tube 10, which serves as the substrate for receiving the hydrogel coatings, may be composed of polyethylene terephthalate (Dacron) or any other suitable material as already described. Preferably the material of the support tube is of open mesh structure to permit complete impregnation of that structure by the hydrogel during the polymerization steps.

After the support tube 10 is completely fitted upon rod 11, the covered rod is placed into a vessel 13 containing the monomer (or comonomers), cross-linking agent, and cosolvent medium. The proportion of water (or other non-solvent for the polymer) in that medium is controlled so that as polymerization proceeds, macrovoids (schematically illustrated in FIGS. 3-5, and designated therein by numeral 14) will be formed. The size and number of such macrovoids may be controlled by regulating the proportion of solvent to non-solvent for the polymer in the system. Polymerization is initiated by irradiation from a cobalt 60 source, the radiation level generally falling within the range of 0.1 to 2.0 Mrads.

In FIG. 3A, the fibrous nature of the porous substrate 10 is diagrammatically depicted to reveal graphically that the liquid reaction mixture 15 invades the interstices of the substrate, extending completely through that substrate to the cylindrical surface of rod 11. Following polymerization, rod 11 is removed and any non-polymerized materials are rinsed away by introducing a solution such as equal volume of water and ethanol into the space formerly occupied by the rod. After soaking the polymer and prosthesis with the cleaning solution for a selected interval of 10 to 30 hours, the rinse solution is removed and a second rod 16 is inserted into the lumen of the support tube. Rod 16 is similar to rod 11 except that it is of smaller diameter with the result that an annular space 17 is provided between the outer surface of rod 16 and the inner surface of the impregnated support tube 10 (FIG. 4). The second polymerizable mixture 15a is then introduced into the annular space, as indicated by the arrows in FIG. 4, the second mixture being essentially the same as the first mixture 15 except for the reduced water content of the solvent system. In the first polymerizable mixture 15, a sufficient amount of water (or other non-solvent for the polymer) was present to cause polymerization in a marginally precipitating medium, with the result that macrovoids 14 were formed, whereas in the second polymerization mixture 15a the water content is reduced so that polymerization proceeds in a solvent medium for the polymer. Consequently, following irradiation and polymerization of the second polymerizable mixture, and removal of rod 16, the substrate 10 is internally coated with a smooth homogenous layer along its inside surface. As diagrammatically illustrated in FIG. 5, the inside layer 15a penetrates some of the macrovoids of outside layer 15, resulting in a smooth transition between the two layers. Ideally, a chemical bonding between such layers also occurs because of their similarity in chemical composition.

Completion of the prosthesis is achieved by withdrawing the substrate and polymer from container 13 and, where necessary, stripping away excessive amounts of polymer along the outer surface of the substrate. The hydrogel impregnated prosthesis is then stored in a suitable solvent (such as equal volumes of water and ethanol) to protect the structure and to leach out unreacted constituents.

It has been found desirable, prior to each of the first and second polymerization steps, to seal vessel 13 and to bubble an inert gas such as nitrogen through the polymerization mixtures, prior to irradiation thereof, to remove oxygen which has the effect of inhibiting polymerization.

The invention is further illustrated by the following examples

EXAMPLE 1

Radiation grafting was used to coat polyethylene terephthalate (Dacron) samples to determine differences in physical characteristics resulting from variations in formulation, with particular emphasis on differences in the proportion of water in the solvent system. The Dacron (U.S. Catheters & Instruments, DeBakey Double Velour) was cut into strips 1 centimeter by 4 centimeters and such strips were cleaned ultrasonically (5 minute wash, 3 rinses) with an aqueous soap solution, and then weighed. Monomer solutions of 10-20% by volume of 2-hydroxyethyl methacrylate (HEMA, Haven Chemical Co., Philadelphia) and ethylene glycol dimethacrylate (EGDMA) of 1-3% were mixed in solvent mixtures consisting either of 50% methanol/50% water or 25% methanol/75% water. Each substrate sample was suspended in a Pyrex test tube to which the polymerizable solution of interest was added. The tubes were then saturated with nitrogen to minimize oxidative reactions and irradiated in a $^{60}Co$ radiation source to receive radiation doses of 0.1 to 0.25 Mrads.

Following polymerization, each sample was dried and weighted, and calculations were made to determine the percent of graft based on the previous weight measurement before treatment. Thereafter, each sample was immersed in water, removed, and again weighed to determine the percent of water imbibed by the gel. Finally, SEM studies were undertaken to measure the macrovoids and microvoids in Feret diameter, and to observe the bead size of the homogenous and heterogenous gels. The following data was developed:

| Formulation | % Graft[1] | % H$_2$O imbibed by gel[2] | Macrovoid size | Microvoid size | Bead size |
| --- | --- | --- | --- | --- | --- |
| 20% HEMA 3.0% EGDMA 0.25Mrad 25% Methanol/75% H$_2$O solvent | 157% | 200% | 20-40µ | 5-10µ | mostly 1-1µ some 5µ |
| 20% HEMA 2.0% EGDMA 0.25Mrad 25% Methanol/75% H$_2$O solvent | 150% | 200% | 20-40µ | 5-15µ | 2-3µ |
| 10% HEMA | | | | | |

-continued

| Formulation | % Graft[1] | % H₂O imbibed by gel[2] | Macrovoid size | Microvoid size | Bead size |
|---|---|---|---|---|---|
| 3% EGDMA 0.25Mrad 50% Methanol/50% H₂O solvent | 93% | 270% | 15–70μ | 5–10μ | 3–4μ |
| 10% HEMA 3.0% EGDMA 0.1Mrad 50% Methanol/50% H₂O solvent | 52% | 315% | 20–30μ | 5–10μ | flakes <1μ centers |
| 20% HEMA 3.0% EGDMA 0.25Mrad 50% Methanol/50% H₂O solvent | 162% | 155% | smooth | <1μ | beads 1–2μ |
| 20% HEMA 2.0% EGDMA 0.25Mrad 50% Methanol/50% H₂O solvent | 161% | 145% | smooth | <1μ | <1μ |
| 20% HEMA 2.0% EGDMA 0.25Mrad 50% Methanol/50% H₂O solvent | 162% | 113% | smooth | .3μ | .1μ |
| 20% HEMA 1.0% EGDMA 0.25Mrad 50% Methanol/50% H₂O solvent | 160% | 120% | smooth | <.8μ | |
| 10% HEMA 2.0% EGDMA 0.25Mrad 50% Methanol/50% H₂O solvent | 89% | 241% | smooth | 1–4μ | .1μ |
| 10% HEMA 1.0% EGDMA 0.25Mrad 50% Methanol/50% H₂O solvent | 95% | 211% | smooth | <.1μ | |

[1] % Graft is $\frac{\text{dry weight of impregnated sample} - \text{original weight}}{\text{original weight}} \times 100$

[2] % Water is $\frac{\text{weight of water imbibed}}{\text{weight of grafted sample}} \times 100$ With regard to heterogenous gel coatings represented by the first four entries, it is apparent that with high water (75% volume) solvent and 20% volume HEMA formulations, in which the weight percent of water in the polymerization mixture was well above 45%, fairly uniform macrovoids of 20 to 40 microns are found with polymer beads of the size 1 to 2 microns. Some bead form aggregates on the order of 5 to 8 microns. The microvoids between such beads are generally of the order of 5 to 10 microns in Feret diameter.

Changing the concentration (2 to 3%) of the cross-linker EGDMA in the 20% HEMA formulations in 75% water solvent did little to change the properties of the gel, as demonstrated by the first two entries of the table. However, there was a marked influence of the cross-linking agent with concentrations of HEMA at 10% in the 50% water solvent. Below 3% EGDMA, a transparent smooth gel was formed with bead sizes of the order of 0.1 micron, whereas at 3% EGDMA in the 10% HEMA, 50% water solvent mixture the heterogenous gel is formed with a bead size of the order of 3 to 4 microns and macropores of 15 to 70 microns Feret diameter.

With regard to homogenous gel coatings, smooth gel coatings were formed with formulations of 40% HEMA, 1 to 3% EGDMA, in a 50% water/50% methanol solvent. No significant differences were observed with the changes in cross-linking concentrations. Bead sizes were uniformly less than 1 micron and spaces between the beads less than 0.8 microns in Feret diameter.

EXAMPLE 2

The results of adjusting the proportion of solvent to non-solvent for the polymer in a polymerization mixture utilizing HEMA as the monomer, EGDMA as the cross-linker, and methanol and water as the constituents in a cosolvent medium, are evident from the following data. All of the polymers of Group A appeared from gross observation as translucent gels. Under SEM observation, such hydrogels were smooth and homogenous, having no apparent macrovoids and having microvoids of a maximum size well under 20 microns Feret diameter. On the other hand, the hydrogels of Group B appeared white and opaque and, under SEM examination, were found to be of heterogenous structure with macrovoids above 20 microns (Feret diameter) as well as microvoids similar to those observed in the hydrogels of Group A.

| Polymerization Mixture and Treatment | Formulation | Weight of Substituents | Wt. % | Vol. % |
|---|---|---|---|---|
| | | Group A | | |
| 20% HEMA | 20 mls HEMA added | HEMA 21.43 grams | 24% | 20% |
| 3% EGDMA | 3 mls EGDMA added | EGDMA 3.071 grams | 3.4% | 3% |
| 0.25Mrad | 77 mls of the 80/20 | Methanol 48.75 grams | 55% | 61.6% |
| 80% Methanol/20% H₂O | ratio cosolvent added | H₂O 15.39 grams | 17.6% | 15.4% |
| 20% HEMA | 20 mls HEMA | HEMA 21.43 grams | 23% | 20% |

-continued

| Polymerization Mixture and Treatment | Formulation | Weight of Substituents | Wt. % | Vol. % |
|---|---|---|---|---|
| 3% EGDMA | 3 mls EGDMA | EGDMA 3.071 grams | 3.3% | 3% |
| 0.25Mrad | 77 mls of 60/40 ratio | Methanol 36.56 grams | 39.7% | 46.2% |
| 60% Methanol/40% $H_2O$ | of cosolvent | $H_2O$ 30.77 grams | 34% | 30.8% |
| 20% HEMA | 20 mls HEMA | HEMA 21.43 grams | 22.9% | 20% |
| 3% EGDMA | 3 mls EGDMA | EGDMA 3.071 grams | 3.3% | 3% |
| 0.25Mrad | 77 mls of 50/50 ratio | Methanol 30.47 grams | 32.6% | 38.5% |
| 50% Methanol/50% H hd 2O | of cosolvent | $H_2O$ 38.47 grams | 41.2% | 38.5% |

| Group B | | | | |
|---|---|---|---|---|
| 20% HEMA | 20 mls HEMA | HEMA 21.43 grams | 22.5% | 20% |
| 3% EGDMA | 3 mls EGDMA | EGDMA 3.071 grams | 3.2% | 3% |
| 0.25Mrad | 77 mls of 40/60 ratio | Methanol 24.38 grams | 25.6% | 30.8% |
| 40% Methanol/60% $H_2O$ | of cosolvent | $H_2O$ 46.16 grams | 48.7% | 46.2% |
| 20% HEMA | 20 mls HEMA | HEMA 21.43 grams | 21.9% | 20% |
| 3% EGDMA | 3 mls EGDMA | EGDMA 3.071 grams | 3.2% | 3% |
| 0.25Mrad | 77 mls of 25/75 ratio | Methanol 15.28 grams | 15.7* | 19.5% |
| 25% Methanol/75% $H_2O$ | cosolvent mix | $H_2O$ 57.70 grams | 59.2% | 57.5% |
| 20% HEMA | 20 mls HEMA | HEMA 21.43 grams | 21.8% | 20% |
| 3% EGDMA | 3 mls EGDMA | EGDMA 3.071 grams | 3.1% | 3% |
| 0.25Mrad | 77 mls of 20/80 ratio | Methanol 12.19 grams | 12.4% | 15.4% |
| 20% Methanol/80% H hd 2O | cosolvent mix | $H_2O$ 61.55 grams | 62.7% | 61.6% |

Translucent gels having appearances similar to those found in the hydrogels of Group A, but prepared with polymerization mixtures having different substituents for the cosolvent systems, were prepared as follows:

On the other hand, by increasing the proportion of that substitutent of the solvent system which is a non-solvent for the polymer (i.e., above the levels given in Group C), polymers of heterogenous structure, having

| Group C | | | | |
|---|---|---|---|---|
| Polymerization Mixture and Treatment | Formulation | Weight of Substituents | Wt. % | Vol. % |
| 20% HEMA | 20 mls HEMA | HEMA 21.43 grams | 24.2% | 20% |
| 3% EGDMA | 3% EGDMA | EGDMA 3.071 grams | 3.5% | 3% |
| 0.25Mrad | 77 mls of 80/20 ratio | Ethanol 48.62 grams | 54.9% | 61.6% |
| 80% Ethanol/20% $H_2O$ | cosolvent | $H_2O$ 15.39 grams | 17.4% | 15.4% |
| 20% HEMA | 20 mls HEMA | HEMA 21.43 grams | 23.4% | 20% |
| 3% EDGMA | 3 mls EGDMA | EGDMA 3.071 grams | 3.4% | 3% |
| 0.25Mrad | 77 mls of 60/40 ratio | Ethanol 36.47 grams | 39.8% | 46.2% |
| 60% Ethanol/40% H hd 2 1 O | of cosolvent | $H_2O$ 30.77 grams | 33.4% | 30.8% |
| 20% HEMA | 20 mls HEMA | HEMA 21.43 grams | 22.9% | 20% |
| 3% EGDMA | 3 mls EGDMA | EGDMA 3.071 grams | 3.3% | 3% |
| 0.5Mrad | 77 mls of 40/60 ratio | Dioxane 31.8 grams | 33.9% | 30.8% |
| 40% Dioxane 60% 1-Butanol/ | of cosolvent | 1-Butanol 37.4 grams | 39.9% | 46.2% |
| 20% HEMA | 20 mls HEMA | HEMA 21.43 grams | 22.1% | 20% |
| 3% EGDMA | 3 mls EGDMA | EGDMA 3.071 grams | 3.2% | 3% |
| 0.5 Mrad | 77 mls of 60/40 ratio | Dioxane 47.76 | 49.0% | 46.2% |
| 60% Dioxane 40% 1-Butanol/ | of cosolvent | 1-Butanol 24.94 grams | 25.7% | 30.8% | a white opaque appearance, may be obtained as follows:

| Group D | | | | |
|---|---|---|---|---|
| Polymerization Mixture and Treatment | Formulation | Weight of Substituents | Wt. % | Vol. % |
| 20% HEMA | 20 mls HEMA | HEMA 21.43 grams | 22.6% | 20% |
| 3% EGDMA | 3 mls EGDMA | EDGMA 3.071 grams | 3.2% | 3% |
| 0.25Mrad | 77 mls of 40/60 ratio | Ethanol 24.31 grams | 25.6% | 30.8% |
| 40% Ethanol/60% $H_2O$ | of cosolvent | $H_2O$ 46.16 grams | 48.6% | 46.2% |
| 20% HEMA | 20 mls HEMA | HEMA 21.43 grams | 21.8% | 20% |
| 3% EGDMA | 3 mls EDGMA | EGDMA 3.071 grams | 3.1% | 3% |
| 0.25Mrad | 77 mls of 20/80 ratio | Ethanol 12.16 grams | 12.4% | 15.4% |
| 20% Ethanol/80% $H_2O$ | of cosolvent | $H_2O$ 61.55 grams | 62.7% | 61.6% |
| 20% HEMA | 20 mls HEMA | HEMA 21.43 grams | 23.7% | 20% |
| 3% EGDMA | 3 mls EGDMA | EGDMA 3.071 grams | 3.4% | 3% |
| 0.5Mrad | 77 mls of 20/80 ratio | Dioxane 15.92 grams | 17.6% | 15.4% |
| 20% Dioxane | of cosolvent | 1-Butanol 49.88 grams | 55.3% | 61.6% |

| Polymerization Mixture and Treatment | Formulation | Group D -continued Weight of Substituents | Wt. % | Vol. % |
|---|---|---|---|---|
| 80% 1-Butanol/ | | | | |

While in the foregoing we have disclosed an embodiment of the invention in considerable detail for purposes of the invention, it will be understood by those skilled in the art that many of these details may be varied without departing from the spirit and scope of the invention.

We claim:

1. A vascular prosthesis comprising a flexible support tube having a porous homogenous hydrogel layer along the inside thereof and a porous heterogenous hydrogel layer along the outside thereof, said homogenous layer having pores of a maximum size less than 20 microns Feret diameter, and said heterogenous layer having pores of the same size as said homogenous layer and in addition having larger pores of a Feret diameter within the range of 20 to 200 microns.

2. The prosthesis of claim 1 in which said pores of said homogenous layer have a maximum size less than 10 microns in Feret diameter.

3. The prosthesis of claim 1 in which said larger pores of said heterogenous layer all have Feret diameters above 30 microns.

4. The prosthesis of claim 1 in which the hydrogel of said homogenous layer has the same chemical composition as the hydrogel of said heterogenous layer.

5. The prosthesis of claim 4 in which said hydrogel is a sparingly cross-linked polymer of hyroxyalkyl methacrylate.

6. The prosthesis of claim 5 in which said hydroxyalkyl methacrylate is 2-hydroxyethyl methacrylate.

7. The prosthesis of claim 6 in which said polymer is sparingly cross-linked by ethylene glycol dimethacrylate.

8. The prosthesis of claim 1 in which the inside diameter of said tube falls within the general range of 1 to 30 millimeters.

9. The prosthesis of claim 8 in which said tube has an inside diameter under 10 millimeters.

10. The prosthesis of claim 8 in which said tube has a wall thickness within the range of 0.5 to 1.5 millimeters.

11. A vascular prosthesis comprising a flexible support tube having an inside diameter within the range of 1 to 30 millimeters and having a wall of open mesh construction with openings extending therethrough, a porous homogenous hydrogel layer secured to and extending along the inside of said tube and a porous heterogenous hydrogel layer secured to and extending along the outside of said tube, said homogeneous layer having pores extending therethrough of a maximum size less than 20 microns Feret diameter, and said heterogenous layer having pores of the same size as said homogenous layer and in addition having larger pores of a Feret diameter within the range of 20 to 200 microns, said inner and outer hydrogel layers extending into the openings of said wall of said tube.

12. The prosthesis of claim 11 in which said heterogenous hydrogel layer extends into the openings in the wall of said tube and contacts said homogenous hydrogel layer.

13. The prosthesis of claim 12 in which said homogenous hydrogel layer extends into at least some of the larger pores of said heterogenous hydrogel layer.

14. The prosthesis of claim 12 in which said homogenous and heterogenous hydrogel layers are of substantially the same chemical composition.

15. The prosthesis of claim 14 in which said hydrogel of said homogenous and heterogenous layers is a sparingly cross-linked polymer of hydroxyalkyl methacrylate.

16. The prosthesis of claim 15 in which said hydroxyalkyl methacrylate is 2-hydroxyethyl methacrylate.

17. The prosthesis of claim 16 in which said polymer is sparingly cross-linked by ethylene glycol dimethacrylate.

18. The prosthesis of claim 11 in which said flexible support tube is formed from a material selected from the group consisting of polyethylene terephthalate, polytetrafluoroethylene, polyethylene, poly-E-caprolactone, poly(glycolic acid), poly (lactic acid), and poly(hydroxy butyric acid).

19. The prosthesis of claim 11 in which said pores of said homogenous layer are less than 10 microns Feret diameter.

20. The prosthesis of claim 11 in which said larger pores of said heterogenous layers have Feret diameters under 30 microns.

21. The prosthesis of claim 11 in which said tube has a wall thickness within the range of 0.5 to 1.5 millimeters.

22. A method for making a vascular prosthesis, comprising the steps of impregnating a porous flexible support tube with a polymerizable mixture of a monolefinic monomer and a minor proportion of a cross-linking agent dissolved in a first cosolvent medium comprising a first constituent in which both the monomer and polymer are readily soluble and a second constituent in which said monomer is soluble but said polymer is substantially insoluble, said second constituent exceeding 45% by weight of said polymerizable mixture, polymerizing said monomer in said first cosolvent medium to provide a cross-linked heterogenous hydrogel having a microstructure characterized by both microvoids and macrovoids, coating the interior of said tube with a second polymerizable mixture of the same monomer and cross-linking agent in a second cosolvent medium containing the same constituents as said first cosolvent medium but wherein said second constituent is less than 45% by weight of the polymerizable mixture, and polymerizing said monomer of said second mixture to produce a smooth hydrogel lining for said tube having a homogenous microstructure substantially free of macrovoids.

23. The method of claim 22 in which said monomer is hydroxyethyl methacrylate.

24. The method of claim 22 in which said first constituent of said cosolvent medium is selected from the group consisting of methanol, ethanol, dioxane, dimethyl formamide, tetrahydrofuryl alcohol, ethylene glycol monomethyl ether, ethylene glycol monoethyl ether, dimethyl sulfoxide, and 2,2,3,3-tetrafluoropropanol.

25. The method of claim 22 in which said second constituent of said cosolvent medium is selected from the group consisting of water and 1-butanol.

26. The method of claim 22 in which said step of coating the interior of said tube includes contacting said heterogenous hydrogel with said second polymerizable mixture.

27. The method of claim 26 wherein said second polymerizable mixture invades at least some of the macrovoids of said heterogenous hydrogel.

28. The method of claim 22 in which said porous flexible support tube is formed of a material selected from the group consisting of polyethylene terephthalate, polytetrafluoroethylene, polyethylene, poly-E-caprolactone, poly(glycolic acid), poly(lactic acid), and poly(hydroxy butyric acid).

29. A method for making a vascular prosthesis, comprising the steps of impregnating a porous flexible support tube with a polymerizable mixture of a water-soluble monolefinic monomer and a minor proportion of a cross-linking agent dissolved in a first solvent consisting essentially of water and a water-miscible organic solvent, said water exceeding 45% by weight of said mixture, polymerizing said monomer in said first solvent to produce a cross-linked heterogenous hydrogel having a microstructure characterized by both microvoids and macrovoids, coating the interior of said tube with a second polymerizable mixture of the same monomer and cross-linking agent in a second solvent containing the same components as said first solvent but wherein the water content is less than 45% by weight of said second mixture, and polymerizing said monomer of said second mixture to produce a smooth hydrogel lining for said tube having a homogenous microstructure substantially free of macrovoids.

30. The method of claim 29 in which said monomer is hydroxyethyl methacrylate.

31. The method of claim 29 in which said organic solvent is selected from the group consisting of methanol, ethanol, dimethyl formamide, tetrahydrofuryl alcohol, ethylene glycol monomethyl ether, ethylene glycol monoethyl ether, dimethyl sulfoxide, and 2,2,3,3-tetrafluoropropanol.

32. The method of claim 29 in which said step of coating the interior of said tube includes contacting said heterogenous hydrogel with said second polymerizable mixture.

33. The method of claim 32 wherein said second polymerizable mixture invades at least some of the macrovoids of said heterogenous hydrogel.

34. The method of claim 29 in which said porous flexible support tube is formed of a material selected from the group consisting of polyethylene terephthalate, polytetrafluoroethylene, polyethylene, poly-E-caprolactone, poly(glycolic acid), poly(lactic acid), and poly(hydroxybutyric acid).

* * * * *